(12) United States Patent
Giles et al.

(10) Patent No.: US 10,600,627 B2
(45) Date of Patent: Mar. 24, 2020

(54) HYBRID MASS SPECTROMETER

(71) Applicant: Micromass UK Limited, Wilmslow (GB)

(72) Inventors: Kevin Giles, Stockport (GB); David J. Langridge, Macclesfield (GB); Steven Derek Pringle, Darwen (GB); Keith Richardson, High Peak (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 301 days.

(21) Appl. No.: 15/314,359

(22) PCT Filed: May 29, 2015

(86) PCT No.: PCT/GB2015/051571
§ 371 (c)(1),
(2) Date: Nov. 28, 2016

(87) PCT Pub. No.: WO2015/181566
PCT Pub. Date: Dec. 3, 2015

(65) Prior Publication Data
US 2017/0200594 A1    Jul. 13, 2017

(30) Foreign Application Priority Data

May 30, 2014  (EP) .................................... 14170549
May 30, 2014  (GB) .................................... 1409586.3

(51) Int. Cl.
*H01J 49/00* (2006.01)
*H01J 49/06* (2006.01)
(Continued)

(52) U.S. Cl.
CPC .......... *H01J 49/004* (2013.01); *G01N 27/622* (2013.01); *H01J 49/0009* (2013.01);
(Continued)

(58) Field of Classification Search
None
See application file for complete search history.

(56) References Cited

U.S. PATENT DOCUMENTS 6,800,846 B2    10/2004   Bateman et al.
6,992,283 B2 *  1/2006   Bateman .............. G01N 27/622
                                                 250/281
(Continued)

FOREIGN PATENT DOCUMENTS

EP    1378930         1/2004
EP    2558850 A1 *    2/2013    .......... G01N 27/622
(Continued)

OTHER PUBLICATIONS

XP055206729, http://www.elta90.com/wp-content/uploads/2011/08/SYNAPT-G2-S-Brochurepdf (Jun. 2011).
(Continued)

*Primary Examiner* — Andrew Smyth

(57) ABSTRACT

A method of mass spectrometry is disclosed comprising separating ions temporally in a first device and analysing the mass or mass to charge ratio of the ions or of product or fragment ions derived from the ions in a mass or mass to charge ratio analyser disposed downstream of the first device. The method further comprises obtaining a first set of drift times for the ions through the first device by measuring ion arrival times and determining the transit time of the ions and/or of the product or fragment ions through one or more intermediate regions or devices disposed between the first device and the mass to charge ratio analyser. The method further comprises obtaining a second set of drift times for the ions through the first device by correcting the first set of drift times to account for the determined transit times.

17 Claims, 9 Drawing Sheets

(51) Int. Cl.
   *G01N 27/62* (2006.01)
   *H01J 49/40* (2006.01)
(52) U.S. Cl.
   CPC ........ *H01J 49/0031* (2013.01); *H01J 49/062* (2013.01); *H01J 49/066* (2013.01); *H01J 49/067* (2013.01); *H01J 49/40* (2013.01)

(56) References Cited

U.S. PATENT DOCUMENTS

| | | | |
|---|---|---|---|
| 6,992,284 | B2 | 1/2006 | Schultz et al. |
| 7,586,088 | B2 * | 9/2009 | Bateman ............... H01J 49/004 |
| | | | 250/281 |
| 7,622,711 | B2 | 11/2009 | Wildgoose et al. |
| 8,629,409 | B2 | 1/2014 | Kovtoun |
| 8,748,811 | B2 | 6/2014 | Okumura |
| 8,822,914 | B2 | 9/2014 | Goshawk |
| 9,281,171 | B2 | 3/2016 | Bateman et al. |
| 9,484,194 | B2 | 11/2016 | Brown et al. |
| 2002/0030159 | A1 | 3/2002 | Chernushevich et al. |
| 2004/0026611 | A1 * | 2/2004 | Bateman ............... H01J 49/062 |
| | | | 250/281 |
| 2004/0026613 | A1 * | 2/2004 | Bateman ............... H01J 49/004 |
| | | | 250/281 |
| 2004/0113064 | A1 * | 6/2004 | Fuhrer ................. G01N 27/622 |
| | | | 250/287 |
| 2007/0014382 | A1 | 1/2007 | Shakeshaft et al. |
| 2011/0168880 | A1 | 7/2011 | Ristroph et al. |
| 2013/0218478 | A1 | 8/2013 | Campuzano et al. |
| 2013/0306855 | A1 * | 11/2013 | Raptakis ............... H01J 49/025 |
| | | | 250/282 |
| 2014/0048704 | A1 * | 2/2014 | Bateman ............... G01N 27/622 |
| | | | 250/282 |
| 2015/0219598 | A1 * | 8/2015 | Mordehai ............. G01N 27/622 |
| | | | 250/282 |
| 2015/0276746 | A1 * | 10/2015 | Li ..................... G01N 33/57434 |
| | | | 514/789 |

FOREIGN PATENT DOCUMENTS

| | | | | |
|---|---|---|---|---|
| EP | 2558850 | A1 * | 2/2013 | ........... G01N 27/622 |
| EP | 2558850 | B1 * | 3/2017 | ........... G01N 27/622 |
| EP | 2558850 | B1 * | 3/2017 | ........... G01N 27/622 |
| GB | 2400231 | | 10/2004 | |
| GB | 2512738 | | 10/2014 | |
| WO | WO 2011128703 | A1 * | 10/2011 | ........... G01N 27/622 |
| WO | WO-2011128703 | A1 * | 10/2011 | ........... G01N 27/622 |
| WO | 2013/140132 | | 9/2013 | |

OTHER PUBLICATIONS

Shvartsburg, A. et al., *"Fundamentals of Traveling Wave Ion Mobility Spectrometry"*, Analytical Chemistry, vol. 80, No. 24, pp. 9689-9699, (Dec. 2008).

Koeniger, S. L. et al., *"Resolution and Structural Transitions of Elongated States of Ubiquitin"*, Journal of the American Society for Mass Spectrometry, vol. 18, pp. 322-331, (2007).

May, J. C. et al., *"Conformational Ordering of Biomolecules in the Gas Phase: Nitrogen Collision Cross Sections Measured on a Prototype High Resolution Drift Tube Ion Mobility-Mass Spectrometer"*, Analytical Chemistry, vol. 86, pp. 2107-2116, (2014).

Ruotolo, B. T. et al., *Peak Capacity of Ion Mobility Mass Spectrometry: Separation of Peptides in Helium Buffer Gas*, Journal of Chromatography B, vol. 782, pp. 385-392 (2002).

Thalassinos, K. et al., *"Ion Mobility Mass Spectrometry of Proteins in a Modified Commercial Mass Spectrometer"*, International Journal of Mass Spectrometry, vol. 236, pp. 55-63, (2004).

* cited by examiner

HYBRID MASS SPECTROMETER

CROSS-REFERENCE TO RELATED APPLICATIONS

This application represents the U.S. National Phase of International Application No. PCT/GB2015/051571 entitled "Hybrid Mass Spectrometer" filed 29 May 2015, which claims priority from and the benefit of United Kingdom patent application No. 1409586.3 filed on 30 May 2014 and European patent application No. 14170549.1 filed on 30 May 2014. The entire contents of these applications are incorporated herein by reference

FIELD OF THE PRESENT INVENTION

The present invention relates generally to mass spectrometry and in particular to a hybrid instrument combining mass separation with a second dimension of separation e.g. ion mobility separation ("IMS").

BACKGROUND

The coupling of ion mobility separation ("IMS") and mass spectrometry ("MS") in commercial instruments has provided useful tools across a wide range of analytical areas.

A known combined ion mobility separation Time of Flight mass spectrometer and method of operating such is disclosed in U.S. Pat. No. 6,992,283 (Micromass) wherein two dimensional (i.e. drift time and mass to charge ratio) nested data sets are generated. Since the timescale for time of flight separation is relatively short, multiple mass to charge ratio analyses can be performed during the course of a single ion mobility separation run.

Other known IMS-MS instruments are disclosed in WO 2005/043115 (Ionwerks), GB-2512738 (Micromass) and US 2014/048704 (Micromass). In US 2014/048704 (Micromass) ions exiting an ion mobility separation device are interfaced with a Time of Flight mass analyser using a travelling wave ion guide.

US 2007/0114382 (Clemmer) discloses an ion mobility separation-mass spectrometry instrument containing two adjacent drift regions.

A general consideration when coupling ion mobility separation and mass spectrometry is that the instrument must operate over markedly different pressure regimes. Typically, ion mobility separation devices are operated at pressures ranging from atmospheric pressure down to 0.1 mbar whereas mass analysers are typically operated at pressures less than $10^{-4}$ mbar. An intermediate ion transfer region is commonly provided which may include an ion guide. The intermediate ion transfer region may include a number of differentially pumped low or intermediate pressure regions operated at pressures between that at which the ion mobility separator and the mass analyser are operated. The intermediate pressure ion transfer region may also contain ion focussing optics which are used to condition the ion beam for mass analysis.

Other multi-stage mass spectrometer geometries are known. For instance, it is known to combine quadrupole analysers or filters with other separation devices.

US 2013/0214146 (Shimadzu) discloses a triple quadrupole instrument where a time delay introduced by a collision cell is used to obtain a relationship between the voltages applied to the first stage quadrupole and the mass to charge ratio of ions selected. This relationship can be used to calibrate neutral loss measurements.

GB-2512738 (Micromass) discloses adjusting a transit time through an interface ion guide to allow the mass filtering characteristics of a quadrupole to be switched.

GB-2421844 (Micromass) discloses a mass spectrometer comprising a travelling wave ion guide arranged downstream of a mass selective ion trap.

US 2012/0193526 (Kovtoun) discloses an ion interface for interfacing an ion trap to a Time of Flight mass analyser comprising multiple confinement cells.

GB-2485667 (Micromass) discloses a method of controlling hydrogen-deuterium exchange on a spectrum by spectrum basis by controlling ion residence times within a travelling wave device.

It is desired to provide an improved mass spectrometer and method of mass spectrometry.

SUMMARY

According to an aspect there is provided a method of mass spectrometry comprising:

separating ions temporally in a first device;

analysing the mass or mass to charge ratio of the ions or of product or fragment ions derived from the ions in a mass or mass to charge ratio analyser disposed downstream of the first device;

obtaining a first set of drift times for the ions through the first device by measuring ion arrival times;

determining the transit time of the ions and/or of the product or fragment ions through one or more intermediate regions or devices disposed between the first device and the mass to charge ratio analyser; and obtaining a second set of drift times for the ions through the first device by correcting the first set of drift times to account for the determined transit times.

It has been recognised that ions take a certain amount of time to transit an intermediate region or device disposed between a separation (first) device and a downstream mass analyser. Conventionally, the additional ion transit times through any intermediate regions between the separation device and the mass analyser are not taken into account when determining the drift times through the separation device. For instance, in the hybrid ion mobility separation-mass spectrometry instrument disclosed in US 2014/048704 (Micromass) the drift times $T_n$ are defined simply as the time between ions being pulsed into the ion mobility spectrometer or separator and the application of the Time of Flight pusher pulse $P_n$.

The drift times determined using known hybrid instruments such as that disclosed in US 2014/048704 (Micromass) and U.S. Pat. No. 6,992,283 (Micromass) thus suffer from a lack of precision as the true ion drift times through the separation device are effectively mis-measured or over-estimated. These additional transit times are typically relatively short compared to conventional ion mobility separator timescales and so the conventional methods still provide a reasonable estimate of the drift times.

The techniques described herein allow for a more accurate determination of ion drift times through a separation device disposed upstream of a mass analyser e.g. in a hybrid mass spectrometer. A more accurate determination of drift times is generally desirable particularly when analysing relatively complex samples containing a number of similar species. By obtaining more accurate values for the drift times through the separation device, improved measurements of drift times per se and/or ion mobilities and/or collision cross sections can be obtained. This is achieved by determining and correcting for the ion transit times through intermediate gas-filled regions or devices situated between the separation device and the mass analyser or detector.

A number of techniques for determining ion transit times through various devices are described herein. These techniques may be implemented by a control system or processor of a mass spectrometer.

It will be appreciated that determining the ion transit times through any particular device is generally not trivial, at least because for some devices the transit times depend on the characteristics of the ions themselves as well as the characteristics of the device. However, it has been recognised that in many cases the ion transit times are deterministic and thus according to the techniques described herein a number of equations or empirical relationships between characteristics of an ion and the resulting transit time through a particular device can be obtained for subsequent use in determining the transit times and/or correcting the drift times. These relationships may be determined as part of a calibration or correction routine or may be calculated e.g. from first principles. The characteristics of the ions may be measured e.g. during the mass analysis and provided as input. Generally, the transit times may be determined according to any of the techniques, equations or relationships described herein.

In either case the transit times and/or corrections may be determined in advance and stored to allow for correction of subsequent experimental cycles. For instance, a general relationship including terms accounting for the additional transit times for each of a particular set of components, including the dependence of the terms on the ion characteristics may be obtained for the purposes of calibrating or correcting subsequent experiments. It will be appreciated, therefore, that the step of determining the transit times may be performed separately and in advance of the steps of separating and analysing the ions. Alternatively, the transit times may be determined dynamically or as part of an experimental cycle.

Determining the transit times may generally comprise determining the transit times of ions through an ion focusing device, wherein the ion focusing device may include a field free region. Determining the transit times may additionally/alternatively comprise determining the transit times through a gas-filled ion transfer region, for example, an RF ion guide, wherein optionally an axial DC gradient or a transient or travelling DC potential may be applied to the ion transfer region in order to urge ions through the device. Determining the transit times may further additionally/alternatively comprise determining ion transit times through a fragmentation or reaction device.

Obtaining the second set of drift times for ions through the first device may comprise correcting the first set of drift times to account for the ion transit times through the one or more intermediate regions or devices, including accounting for the effect of collisions and accelerations within the intermediate regions or devices.

The ion arrival times used to obtain the first set of drift times may be any suitable or well-defined ion arrival time. For instance, the first set of drift times may be determined from ion arrival times at a detector, at a component of the detector or at some other upstream component. In particular, the first set of drift times may be obtained based on the ion arrival times at the extraction or entrance region of the mass analyser e.g. the pusher electrode of an orthogonal acceleration Time of Flight mass analyser as described in US 2014/048704 (Micromass).

The second set of drift times may then generally be obtained by subtracting the determined transit times through the one or more intermediate regions or devices from the first set of drift times. The second set of drift times may thus be determined based on the measured ion arrival times and the determined ion transit times.

It will be appreciated that a mass or mass to charge ratio analyser generally comprises or passes ions onwards towards an ion detector. The mass or mass to charge ratio analyser and the detector may together form a single ion detection system. They may be provided in the form of a single device or as two separate components.

The step of separating ions temporally in the first device may comprise separating ions according to ion mobility.

The first device may comprise an ion mobility separation device. The first device may comprise a drift tube ion mobility separation device or a travelling wave ion mobility separation device. It will be understood that a travelling wave ion mobility separation device is axially segmented so that one or more transient DC voltage waveforms or pulses can be applied in order to translate ions along the device.

In this embodiment, a new method of operating an ion mobility enabled mass spectrometer having one or more post ion mobility separation devices such as gas cells, intermediate pressure ion transfer devices, mass filters and ion transfer optics is provided. The method accounts for the contribution to the measured drift time of the transit times through such devices allowing an accurate determination of the true ion mobility separation drift times and/or collision cross sections.

The techniques described herein may thus be used to obtain improved measurements of ion mobility or collision cross section. In particular, the obtained drift times may be used: (i) to calculate collision cross section and/or ion mobility; and/or (ii) to calibrate drift time against collision cross section and/or ion mobility.

Alternatively/additionally the first device may separate ions according to differential ion mobility, mass or mass to charge ratio.

The transit time of ions through the one or more intermediate regions or devices may be a function of mass or mass to charge ratio and/or ion mobility.

It has been recognised that the transit time of ions through certain gas-filled devices or regions may be dependent on the characteristics of the ions. Thus, even though these intermediate devices or regions are not intended to separate the ions, it will be appreciated that they may potentially introduce mass, mass to charge ratio and/or ion mobility correlated errors that may be corrected for using the techniques described herein to provide a more accurate determination of the drift time through the separation device.

The method may further comprise determining the transit time of ions through one or more intermediate regions or devices disposed between the first device and the mass to charge ratio analyser using the mass or mass to charge ratio analysis.

The method may further comprise determining the transit time of ions through one or more or each of a plurality of intermediate regions or devices.

For instance, in embodiments, there may be: (i) two intermediate regions or devices; (ii) three intermediate regions or devices; (iii) four intermediate regions or devices; or (iv) five or more intermediate regions or devices. Each of the plurality of intermediate regions or devices may correspond to any of the intermediate regions or devices described herein. Furthermore, it is noted that an intermediate region or device may contain multiple regions or devices.

The one or more intermediate regions or devices may generally comprise one or more of: (i) a quadrupole mass filter; (ii) an electrostatic lens; (iii) an ion guide; or (iv) a fragmentation or reaction device, such as a collision cell.

In embodiments, the one or more intermediate regions or devices may comprise one or more differential pumping apertures.

In embodiments the mass spectrometer may comprise:

(i) at least one intermediate pressure region and at least one low pressure region between the first device and the mass or mass to charge ratio analyser; and/or (ii) at least three intermediate regions between the first device and the mass or mass to charge ratio analyser comprising at least one intermediate pressure region and at least one low pressure region; and/or (iii) at least two intermediate pressure regions and at least two low pressure regions between the first device and the mass or mass to charge ratio analyser, wherein the intermediate pressure region(s) is maintained, in use, at a higher pressure than the low pressure region(s).

In an embodiment, the intermediate pressure region may be maintained, in use, at about $10^{-3}$ to $10^{-4}$ mbar and the low pressure region may be maintained, in use, at about $10^{-5}$ mbar or lower.

The method may comprise maintaining the first device at a higher pressure than the mass or mass to charge ratio analyser and maintaining the one or more intermediate region or device at an intermediate pressure between that of the first device and the mass or mass to charge ratio analyser.

In embodiments:

(i) the first device may be maintained at a pressure of about 0.1 mbar to 1000 mbar, and preferably about 0.1-5 mbar; and/or (ii) the intermediate region or device may be maintained at a pressure of about $10^{-3}$-$10^{-4}$ mbar or about $10^{-5}$ mbar; and/or (iii) the mass or mass to charge ratio analyser and the detector may be maintained at a pressure of about $10^{-6}$-$10^{-9}$ mbar or below.

The method may further comprise controlling the operation of one or more devices disposed between the first device and the mass or mass to charge ratio analyser based in part on the determined transit time of ions through the one or more intermediate regions or devices.

It will also be appreciated that precise knowledge of the ion transit times through the various intermediate devices may be used to determine the ion arrival times at an intermediate device. An accurate knowledge of the ion arrival times at any particular device may allow more precise temporal control of that device. The techniques described herein may also therefore provide improved instrument control. It will be appreciated that this improved instrument control may be advantageous in its own right, regardless of whether the determined transit times are also used to correct drift times.

For instance, the determined ion transit times may be used to determine the ion arrival times at a quadrupole device or a collision cell disposed between the separation device and the mass analyser. Knowledge of the ion arrival times may then be used to switch or adjust the operating conditions of the quadrupole device or collision cell.

Similarly, the determined ion transit times may be used to determine the precise ion arrival times at the extraction region of an enhanced duty cycle ("EDC") orthogonal acceleration Time of Flight instrument.

The step of analysing the mass or mass to charge ratio of ions may be performed using a Time of Flight or an orthogonal acceleration Time of Flight mass spectrometer and optionally further comprising operating the Time of Flight mass spectrometer in a nested acquisition mode.

In other embodiments, the mass or mass to charge ratio analyser and/or detector may comprise: (i) a mass to charge ratio filtering device, such as a quadrupole mass filter; (ii) a Fourier Transform mass spectrometer; (iii) a mass analyser having a quadro-logarithmic potential distribution; (iii) a Fourier Transform mass analyser; or (iv) an ion trap.

In cases where the detector is a virtual or Fourier Transform based detector, any references to ion arrival times should be interpreted suitably.

The method may further comprise:

after the step of separating ions temporally in the first device, causing ions to fragment or react; and determining the transit time of parent or precursor ions through an intermediate region or device disposed upstream of the fragmentation or reaction device and/or the transit time of fragment or product ions through an intermediate region or device disposed downstream of the fragmentation or reaction device.

The techniques described herein extend to instruments employing post-ion mobility separation fragmentation. In this case, it is the measured fragment ion drift times or arrival times at the detectors that can be corrected to account for various ion transit times. These embodiments may provide improved measurements of precursor ion drift times, improved instrument control and may facilitate assigning fragment ions to other related precursor or fragment ions.

The method may comprise determining the drift time of parent or precursor ions through the first device in part using the mass or mass to charge ratio of corresponding fragment or product ions.

The method may comprise determining the transit time of a precursor-fragment transition through a fragmentation or reaction device.

It has been recognised that the time and/or axial length at which a precursor or parent ion fragments into a particular fragment ion within a collision cell may be reproducible, and may be specific to that precursor-fragment transition i.e. may contain information relating to the particular precursor and fragment ion masses and structures. Different precursor-fragment transitions may therefore have different ion transit times through a collision cell as the relative time spent passing through the cell as either a precursor ion or a fragment ion will be different. This may be corrected for using the techniques described herein.

Furthermore, the transit times for specific precursor-fragment transitions may contain structural information relating to the precursor ion that may be used to characterize the sample. For example, these times may be stored in a database or library and may be used to subsequently identify or confirm the identity of a particular species. Thus, it may also be desirable to determine the transit time of precursor-fragment transitions through a fragmentation or reaction device regardless of whether or not this information is used to correct the drift time measurements.

The method may further comprise assigning fragment or product ions to corresponding parent or precursor ions or to other related fragment or product ions on the basis of a determined transit time, drift time, ion mobility or gradient.

The transit time of ions through the one or more intermediate regions or devices may be unknown or partially unknown but is reproducible.

For instance, the regions or device may introduce an unknown delay term i.e. one that cannot be derived from first principles or accurately predicted based on the ion characteristics alone. Using the techniques described herein, an empirical determination of this delay term can be made so that the transit time of ions may be determined.

The method may further comprise varying one or more parameters of the first device to determine the transit times.

This may facilitate determining and correcting for reproducible factors which cannot otherwise be accurately predicted. In particular, one or more parameters of the first device may be varied as part of a calibration routine to determine, and hence subsequently correct for, an unknown or partially unknown time delay of the type discussed above. The method may thus comprise varying one or more parameters of the first device to determine the transit times in order to determine an unknown or partially unknown but reproducible transit time. The one or more parameters may, for instance, comprise the applied field, the length of the first device or the number of passes in a multipass or cyclic separation device.

For example, by varying parameters of an ion mobility separation device, unknown and ion mobility separation-independent delays can be accounted for. This may be particularly useful when determining the effective arrival time of precursor-fragment transitions at the ion detection system and hence the parent or precursor ion drift times or ion mobilities based on the measured fragment ion arrival times or drift time profiles. In this case, unknown and/or structurally dependent delays introduced by the fragmentation process can be determined.

According to another aspect there is provided a mass spectrometer comprising:

a first device for separating ions temporally;

a mass or mass to charge ratio analyser disposed downstream of the first device;

one or more intermediate regions or devices disposed between the first device and the mass or mass to charge ratio analyser; and a control system comprising a processor configured:

(i) to obtain a first set of drift times for the ions through the first device by measuring ion arrival times;

(ii) to determine the transit time of the ions and/or of the product or fragment ions through one or more intermediate regions or devices disposed between the first device and the mass to charge ratio analyser; and (iii) to obtain a second set of drift times for the ions through the first device by correcting the first set of drift times to account for the determined transit times.

The control system may be configured to perform any of the method steps described above.

According to another aspect there is provided a method of mass spectrometry comprising:

separating ions temporally in a first device;

analysing the mass or mass to charge ratio of ions in a mass or mass to charge ratio analyser disposed downstream of the first device; and determining the transit time of ions through an one or more intermediate regions or devices disposed between the first device and the mass to charge ratio analyser.

The mass or mass to charge ratio analyser may generally comprise a detector or may pass ions towards a detector and the method may accordingly comprise measuring the ion arrival times at the detector.

As described above, the method may comprise determining the drift times of ions through the first device based in part on the determined transit times of those ions through the one or more intermediate regions or devices. The drift times may be determined based on the determined transit ions in combination with measured ion arrival times at a detector associated with or downstream of the mass or mass to charge ratio analyser.

The step of separating ions temporally in the first device may comprise separating ions according to ion mobility.

The method may further comprise controlling the operation of one or more devices disposed between the first device and the mass or mass to charge ratio analyser based in part on the determined transit time of ions through the one or more intermediate regions or devices.

A determination of the transit times through the one or more intermediate regions or devices may provide an improved instrument control as explained above. The method may comprise controlling a quadrupole device and/or a collision cell and/or an enhanced duty cycle ("EDC") orthogonal acceleration Time of Flight instrument.

The transit times of ions through the one or more intermediate regions or devices may be a function of mass or mass to charge ratio and/or ion mobility.

For instance, the one or more intermediate regions or devices may comprise one or more ion transfer or ion focusing regions as described above.

The method may comprise, after the step of separating ions temporally in the first device, causing ions to fragment or react. The method may further comprise determining the transit time of parent or precursor ions through an intermediate region or device disposed upstream of the fragmentation or reaction device and/or the transit time of fragment or product ions through an intermediate region or device disposed downstream of the fragmentation or reaction device.

The method may comprise determining the drift time of parent or precursor ions through the first device in part using the mass or mass to charge ratio of corresponding fragment or product ions.

The method may comprise determining the transit time of a precursor-fragment transition through a fragmentation or reaction device.

The transit time through the fragmentation or reaction device may contain information relating to the time taken for a particular parent or precursor ion to fragment (into a particular ion) in the device. As explained above, this may yield useful structural information or be used in library searches.

The method may comprise further comprising assigning fragment or product ions to their corresponding parent or precursor ion or to other related fragment or product ions on the basis of a determined transit time, drift time, ion mobility or gradient.

Fragment ions originating from the same parent or precursor ion should share the same drift times through the first device and any devices upstream of the fragmentation cell, and so an accurate determination of the ion transit and drift times may facilitate an improved assignment or confirmation of assignment between parent or precursor and fragment or product ions.

In accordance with a further aspect there is provided a mass spectrometer comprising:

a first device for separating ions temporally;

a mass or mass to charge ratio analyser disposed downstream of the first device;

a detector disposed downstream of or within the mass or mass to charge ratio analyser;

one or more intermediate regions or devices disposed between the first device and the detector; and a control system comprising a processor configured:

(i) to determine the transit time of ions through the one or more intermediate regions or devices.

According to another aspect there is provided a method of mass spectrometry comprising:

separating ions temporally in a first device;

analysing the mass or mass to charge ratio of ions in a mass or mass to charge ratio analyser disposed downstream of the first device and measuring the arrival times of the ions at a detector; and determining the transit time of ions through one or more intermediate regions or devices disposed between the first device and the mass to charge ratio analyser.

The embodiments as described above may generally comprise any or all features described above at least to the extent that they are not mutually incompatible.

According to another aspect there is provided an apparatus for ion mobility-mass spectrometry comprising:

(a) at least one ion mobility separation device arranged upstream of at least one intermediate pressure region, at least one low pressure region, at least one mass to charge ratio analysis device and a detector; where (b) the transit times of an ions through the low pressure region(s) is related to the mass to charge ratio of the ions; and where (c) the mass to charge ratio analysis is used to calculate the transit time of ions through the low pressure region and these transit times are used, in combination with the arrival times at the detector to calculate drift times through the mobility device.

In an embodiment, the mass to charge ratio analysis device comprising a Time of Flight mass analyser operating in a nested acquisition mode.

In another embodiment, the mass to charge ratio analysis device comprises a mass to charge ratio filtering device such as a quadrupole.

In embodiments, the low pressure region incorporates a quadrupole mass filter and/or an electrostatic lens.

In embodiments, the drift time measurement is used to calibrate drift time against collision cross section or ion mobility.

In embodiments, the drift time measurement is used to calculate collision cross section or ion mobility.

In embodiments, the drift time measurement is used to temporally control a device or devices interposed between the ion mobility separation device and the detector such as a quadrupole, collision cell or Enhanced Duty Cycle ("EDC") mass spectrometer.

In embodiments, the ions undergo post-ion mobility separation fragmentation and the drift time of parent or precursor ions are, in part, calculated using the mass to charge ratio of fragment or product ions.

In an embodiment, the parameters of the ion mobility separation are varied so as to allow the determination of precursor or parent drift times or ion mobilities via fragment ion measurements.

In embodiments, the process may be used to associate fragment and parent or precursor ions in a MSMS experiment or an HDMS$^e$ experiment.

According to an embodiment the mass spectrometer may further comprise:

(a) an ion source selected from the group consisting of: (i) an Electrospray ionization ("ESI") ion source; (ii) an Atmospheric Pressure Photo Ionization ("APPI") ion source; (iii) an Atmospheric Pressure Chemical Ionization ("APCI") ion source; (iv) a Matrix Assisted Laser Desorption Ionization ("MALDI") ion source; (v) a Laser Desorption Ionization ("LDI") ion source; (vi) an Atmospheric Pressure Ionization ("API") ion source; (vii) a Desorption Ionization on Silicon ("DIOS") ion source; (viii) an Electron Impact ("EI") ion source; (ix) a Chemical Ionization ("CI") ion source; (x) a Field Ionization ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionization ("DESI") ion source; (xvi) a Nickel-63 radioactive ion source; (xvii) an Atmospheric Pressure Matrix Assisted Laser Desorption Ionization ion source; (xviii) a Thermospray ion source; (xix) an Atmospheric Sampling Glow Discharge Ionization ("ASGDI") ion source; (xx) a Glow Discharge ("GD") ion source; (xxi) an Impactor ion source; (xxii) a Direct Analysis in Real Time ("DART") ion source; (xxiii) a Laserspray Ionization ("LSI") ion source; (xxiv) a Sonicspray Ionization ("SSI") ion source; (xxv) a Matrix Assisted Inlet Ionization ("MAII") ion source; (xxvi) a Solvent Assisted Inlet Ionization ("SAII") ion source; (xxvii) a Desorption Electrospray Ionization ("DESI") ion source; and (xxviii) a Laser Ablation Electrospray Ionization ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionization Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser;

(iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms;

(v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Figure 1:
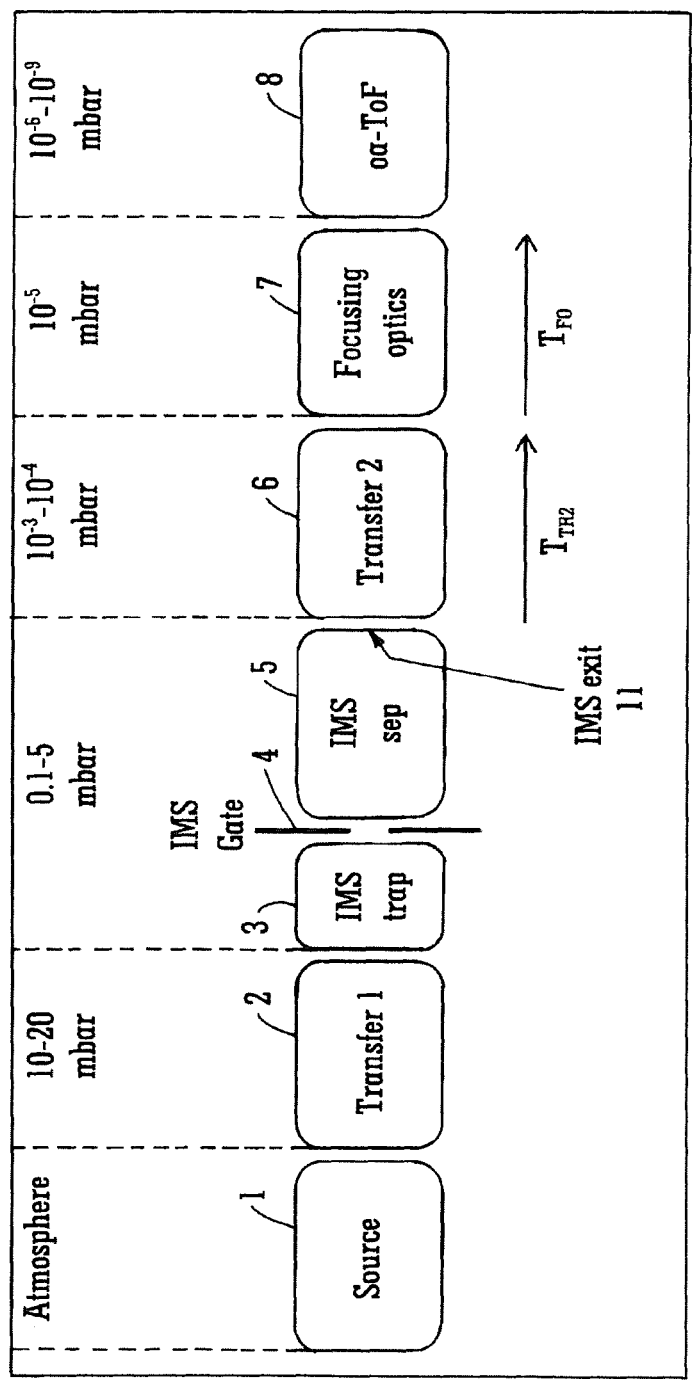
FIG. 1 schematically shows the pressure regimes within a hybrid ion mobility separation-mass spectrometer instrument according to an embodiment.

A first embodiment will now be described. FIG. 1 shows typical operating pressures within different regions of an ion mobility separation-Time of Flight instrument wherein ions move downstream from left to right. The dotted vertical lines indicate separate regions of different pressures. These different pressure regions may generally be separated by differential pumped apertures (not shown).

Ions may be provided at atmospheric pressure by an Electrospray ion source 1. The ions are then transferred through a high pressure (e.g. 10 to 20 mbar) transfer region 2 into an ion mobility separation device. The ion mobility separation device includes an accumulation or trapping region 3, an ion gate 4 and an ion mobility separation region 5 which may comprise a conventional drift tube. These components are, however, not intended to be limiting. Packets of ions are periodically pulsed using the ion gate 4 from the trapping region 3 into the ion mobility separation region 5 where components separate towards the exit 11 of the ion mobility separation device according to their ion mobility. During each ion mobility separation, the ion gate 4 may be closed. Subsequent ions arriving from the upstream devices 2 may be trapped in the trapping region 3 before the ions are released into the ion mobility separation device 5. This approach ensures high duty cycle in operation when compared with traditional non-trapping based gated approaches. The pressure in the ion mobility separation region is typically about 0.1 to 5 mbar.

The ion mobility separation device 5 is coupled to a downstream ion detection system 8 including a mass analysis device and an ion detector. In this embodiment, the ion detection system of the mass spectrometer comprises an orthogonal acceleration Time of Flight ("oaTOF") mass spectrometer which operates at pressures of about $10^{-6}$ to $10^{-9}$ mbar. The ion mobility separation-Time of Flight mass spectrometer may be operated in a nested acquisition mode similar to that described in U.S. Pat. No. 6,992,283 (Micromass).

A number of intermediate or low pressure regions may be disposed between the exit 11 of the ion mobility separation device 5 and the ion detection system 8. In the embodiment illustrated in FIG. 1 these may include an intermediate pressure ion transfer region 6 and ion focusing optics 7 that may condition the ion beam prior to subsequent Time of Flight mass analysis. These components are disposed within separate differentially pumped regions with respective pressures of around $10^{-3}$ to $10^{-4}$ mbar and $10^{-5}$ mbar.

The nature and number of these components and the typical operating pressures is not intended to be limiting. For instance, additional ion transfer, mass filtering, reaction or fragmentation devices may be incorporated at any suitable position or pressure within the instrument.

The ion transfer regions may or may not use RF confinement. However, ions will typically be RF confined in at least the intermediate pressure transfer region 6. The intermediate pressure transfer region 6 may also include a reaction or fragmentation device. For instance, ions may be accelerated into a collision cell to form fragment ions via collisionally induced dissociation ("CID").

The time that ions arrive at the mass analyser 8 is increased over the time at which the ions exited the ion mobility separation device by an amount corresponding to the ion transit time through the intermediate pressure regions. Known instruments such as that disclosed in U.S. Pat. No. 6,992,283 (Micromass) do not take this into account thereby resulting in a mis-measurement of the ion mobility separation drift times.

In order to accurately determine the drift time of ions through the ion mobility separation device 5 using the ions detected at the mass analyser 8, it is necessary to correct for this additional transit time. It has been recognised that these transit times i.e. the time $T_{TR2}$ taken to transit the intermediate pressure transfer region 6, and the time $T_{FO}$ taken to transmit the focusing optics region 7, can depend on the characteristics of the ions.

Embodiments may provide techniques for determining the transit time of ions through the various components disposed between the ion mobility separation device 5 and the mass analyser 8 and hence accurately determining the time at which ions exit the ion mobility separation device 5 and/or arrive at any other components. The transit times are generally deterministic and the relationship between the transit time and certain ion characteristics (e.g. mass to charge ratio, ion mobility) may be described by an equation. Once the form of these equations has been determined, the techniques described herein may be used to implement suitable corrections or calibrations accounting for the additional ion transit times. These corrections or calibrations may, for example, be implemented by a processor as a routine or algorithm.

By way of example, various equations describing the transit times for different components and/or conditions will now be described.

For instance, ions may be electrostatically focused by the ion focusing optics 7 in order to condition the ion beam for subsequent Time of Flight mass analysis. It is generally undesirable for ions to collide with background gas in the focusing optics 7 as this may affect the performance of the Time of Flight mass analyser 8. This requirement, combined with the electrostatic nature of focusing optics results in ions transiting the focusing optics region 7 experiencing substantially the same potential drops and therefore all ions having the same average kinetic energy to charge ratio i.e. ion energy. For focusing optics including field free regions, the transit time, $T_{FO}$, therefore becomes proportional to the square root of mass to charge ratio (Eqn. 1):

$$T_{FO}(m/q) = A\sqrt{m/q} \quad (1)$$

In Eqn. 1, the constant A is related to e.g. the dimensions of spacing between and potentials applied to the focussing optics. Its value can be derived from first principles or may be determined from simulations or calibration experiments. For illustrative purposes, the constant A for the transit time across the focusing optics of a commercial WATERS SYNAPT® ion mobility separation-mass spectrometry instrument is typically $4 \times 10^{-2}$ s $C^{1/2}$ $kg^{-1/2}$. The corresponding flight times for singly charged ions having a mass 2000 Da would be 180 µs and 80 µs for ions having a mass 400 Da i.e. a difference of 100 µs.

A second example is the transit time through transfer regions where the ions can undergo collisions with background or cooling gas, for instance, RF confined multipoles, stacked-ring ion guides ("SRIG") and RF confined or non RF confined ion funnels. In such devices ions must typically be actively propelled in order to minimize the transit time and any axial diffusive spreading. If ions are not actively propelled through the device, the fidelity of the ion mobility separation peaks may be lost. The propulsion can generally adopt any known method.

One method involves applying transient DC voltages, i.e. travelling waves, to an axially segmented RF ion guide to transfer ions through the device. This approach is described, for example, in U.S. Pat. No. 6,800,846 (Micromass). In this approach, all of the ions are transferred in approximately the same time and the transit time is substantially independent of ion characteristics (Eqn. 2):

$$T_{TR2} = \frac{L}{S} \quad (2)$$

wherein L is the length of the transfer region and S is the velocity of the travelling wave. These are both known for a given instrument geometry. A similar expression can be derived for devices where ions are driven by a gas flow instead of a travelling wave. In this case S would relate to the bulk gas flow speed.

Another method involves introducing axial fields along part or all of an RF ion guide. The axial fields can be applied via segmentation of the RF electrodes or by the addition of separate vane electrodes that can be tilted, segmented or have resistively coated surfaces. In this method ions achieve a terminal velocity, $U_T$, related to the applied axial field, E, and their ion mobility, K (Eqn. 3):

$$U_T = KE \quad (3)$$

Ion mobility is related to the ion charge, shape, size as well as cell pressure, etc.

Figure 2:
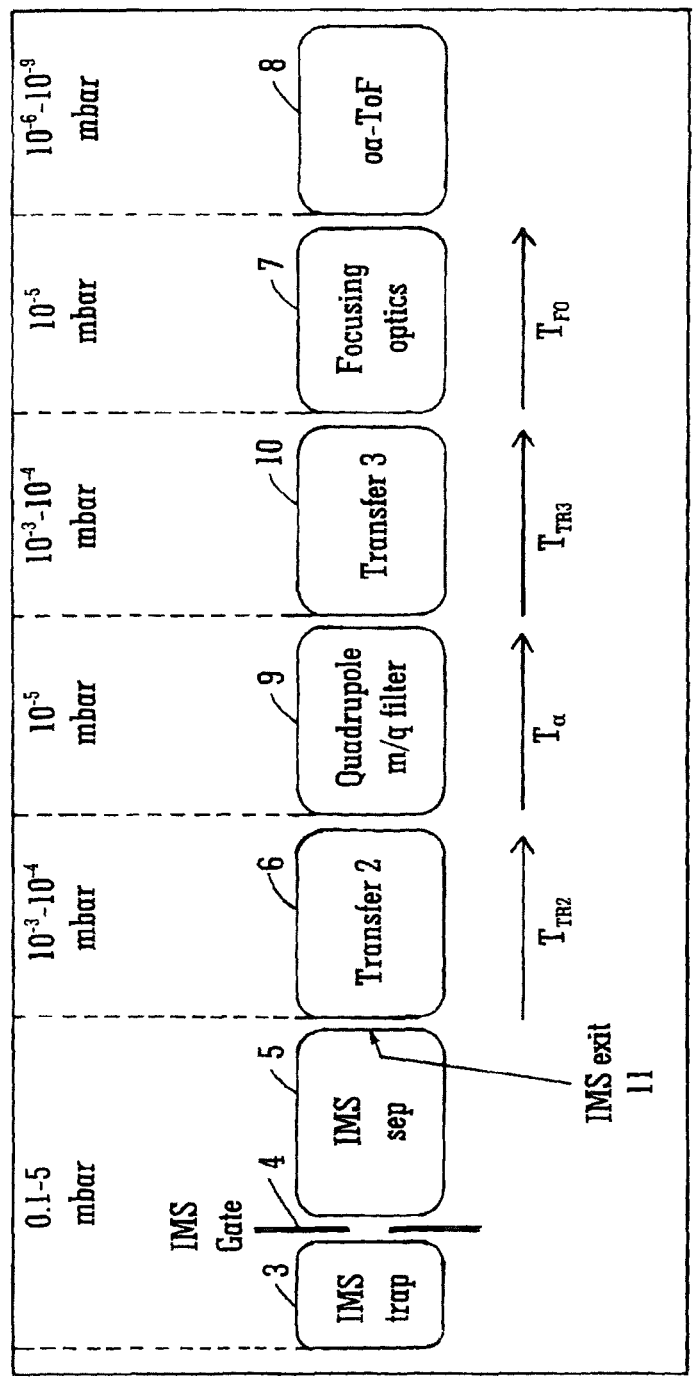
FIG. 2 schematically shows the pressure regimes within another hybrid ion mobility separation-mass spectrometer instrument according to an embodiment.

Eqn. 3 is of course the governing equation for traditional drift tube ion mobility separation devices. However, it takes no account of acceleration or deceleration within the device. Normally, i.e. over the timescale of an ion mobility separation experiment, the time taken to reach terminal velocity tends to be negligible compared with the overall experimental times. However, in some instrument geometries this effect can become significant e.g. when axial fields are used to propel ions through relatively short transfer regions or where the ion mobility separation drift tube is relatively short. FIG. 2 shows a schematic of one such geometry where this effect may be significant.

FIG. 2 shows a similar ion mobility separation device to that described above with relation to FIG. 1 and with like reference numerals representing like components. The upstream source and high pressure transfer regions are not shown. Again, following ion mobility separation, ions are eventually detected by an orthogonal acceleration Time of Flight mass analyser 8.

In the embodiment shown in FIG. 2, ions exiting the ion mobility separation device 5 transit an intermediate pressure transfer region 6, a quadrupole mass filter 9, a further transfer region 10 and ion focussing optics 7. The quadrupole mass filter 9 may operate at about $10^{-5}$ mbar. Generally, the quadrupole device 9 is arranged to be collision free and the transit time of ions across or through it is therefore as described by Eqn. 1.

The velocity of ions, U, in this region tends to be relatively high (see Eqn. 4) so that ions decelerate as they enter the adjacent ion transfer region 10. The further transfer region 10 may operate at pressures around $10^{-3}$ to $10^{-4}$ mbar:

$$U = \sqrt{\frac{2qV}{m}} \quad (4)$$

wherein V is a constant related to the accelerating potentials.

Under these conditions, as described in U.S. Pat. No. 8,426,802 (Micromass), Eqn. 3 may be modified to include time dependent terms as follows:

$$U(t) = KE\left(1 - e^{-\frac{qt}{mK}}\right) + U_0 e^{-\frac{qt}{mK}} \quad (5)$$

wherein $U_0$ is the mass to charge ratio dependent initial velocity of ions entering the region which is governed by Eqn. 4. This equation can be integrated to give the position through the device as a function of time (Eqn. 6):

$$x(t) = KEt + K^2 E \frac{m}{q} \left( e^{-\frac{qt}{mK}} - 1 \right) + U_0 K \frac{m}{q} \left( 1 - e^{-\frac{qt}{mK}} \right) \qquad (6)$$

This equation may apply generally to any gas-filled RF device having an axial field applied across it, including an RF ion mobility separation drift tube or ion transfer region. The transit time across such a device can be determined from Eqn. 6 by setting x(t) to be the length of the RF ion guide and solving for t. In this case it can be seen that the transit time, $T_{TR3}$, through the transfer region 10 disposed downstream of the quadrupole mass filter 9 is a function of both ion mobility and mass to charge ratio.

Eqn. 6 can be solved for t in many different ways, for instance including numerical approaches or analytical approaches using the Lambert W function (also referred to as the Omega function or product logarithm). Other approximate solutions can also be considered. For instance, in cases when the device transit time, $t_d \gg mK/q$, Eqn. 6 approximates to Eqn. 7:

$$x(t) = KEt_d - K^2 E \frac{m}{q} + U_0 K \frac{m}{q} \qquad (7)$$

Setting x(t) in Eqn. 7 to L and solving for $t_d$ reveals:

$$t_d = \frac{L + K^2 E \frac{m}{q} - U_0 K \frac{m}{q}}{KE} \qquad (8)$$

If ion accelerations are not accounted for, the transit time would be L/KE. Under these conditions therefore Eqn. 8 can be interpreted as a mobility and mass to charge ratio dependent shortening of the RF device.

Figure 3A:
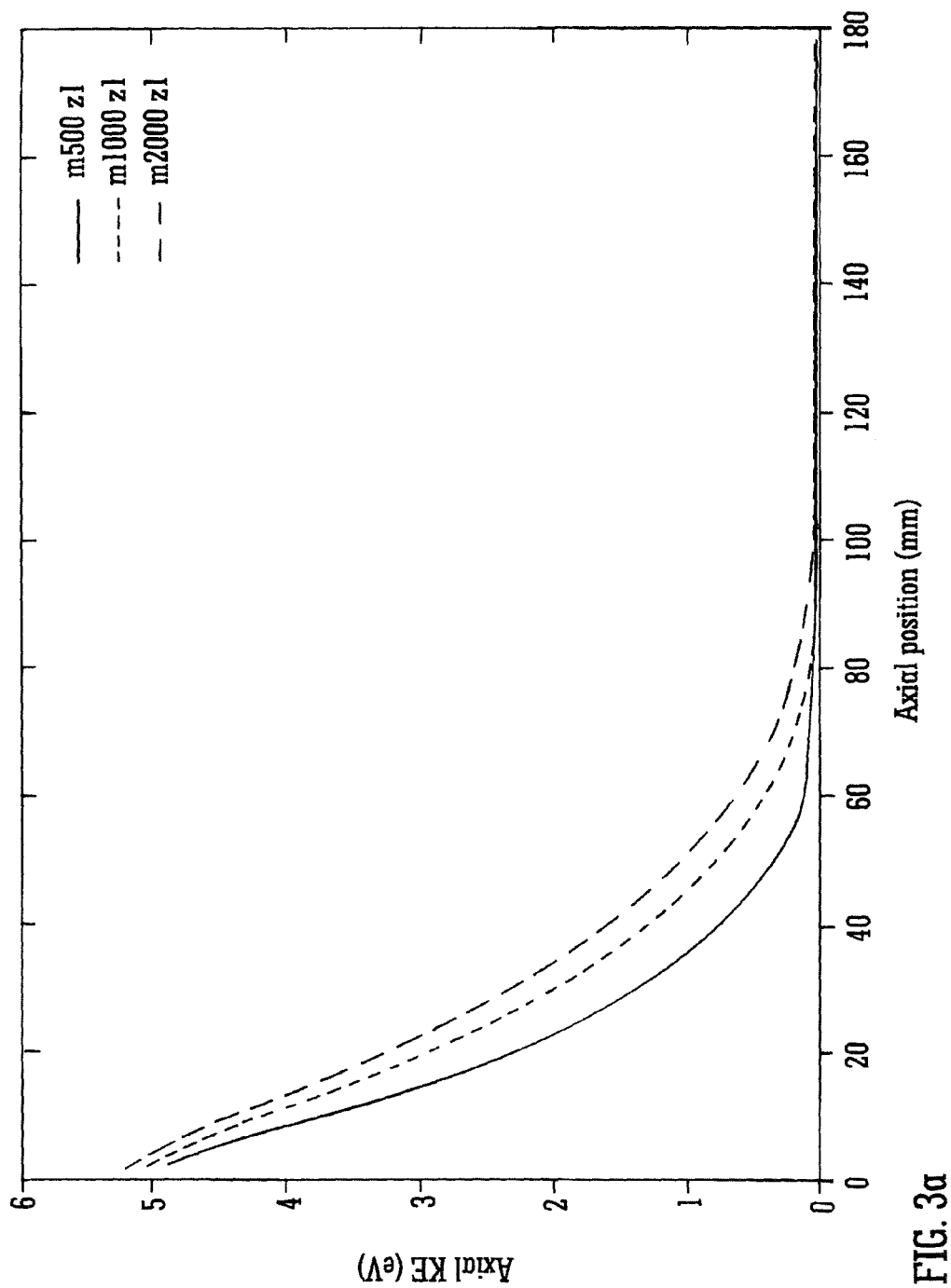
FIG. 3A shows the ion axial kinetic energy as a function of axial position within a gas-filled axial RF ion guide and FIG. 3B shows the axial ion velocity as a function of normalised time within the gas-filled axial RF ion guide.
Figure 3B:
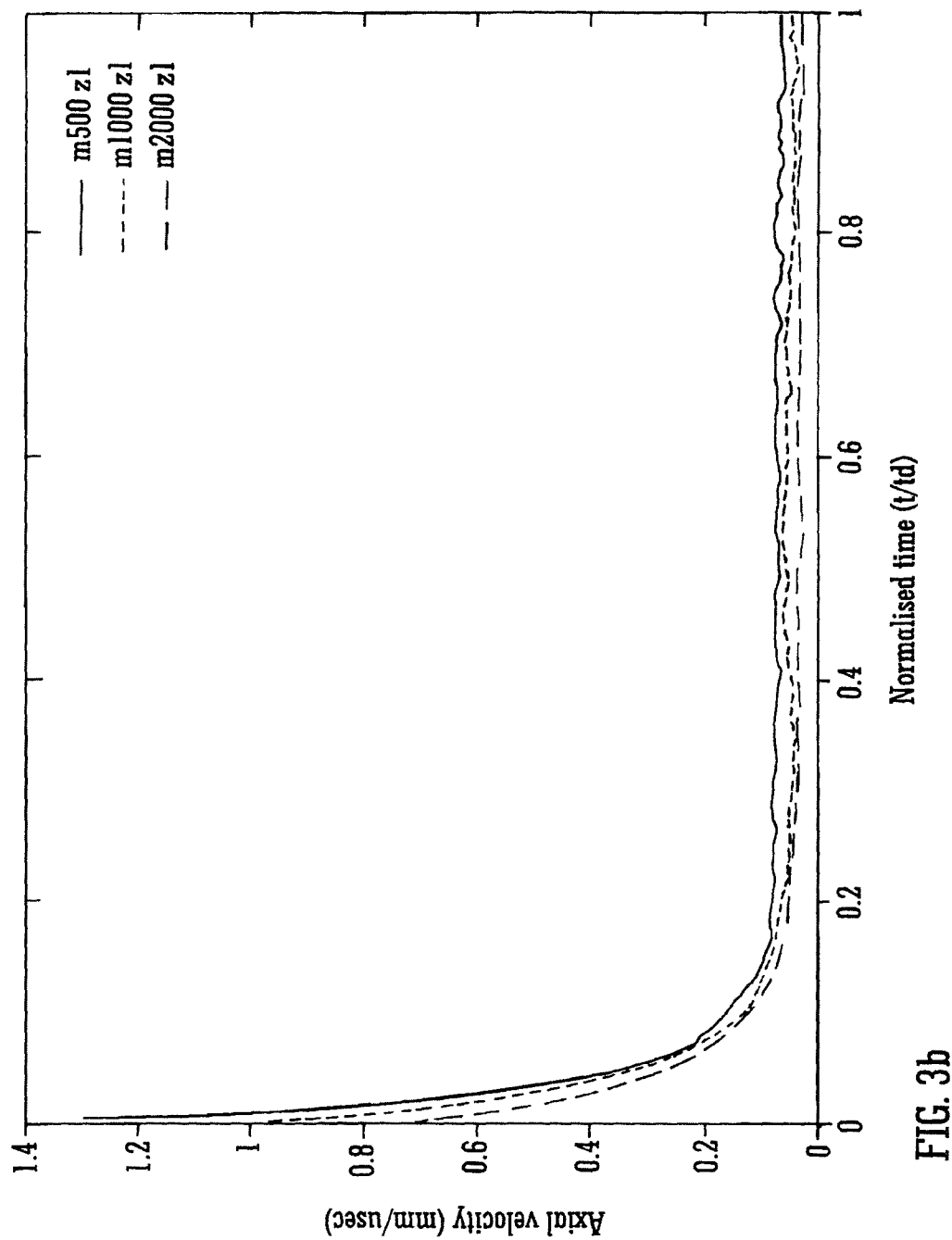

FIGS. 3A and 3B show SIMION® simulations for three singly charged components of different mass to charge ratio injected into a gas-filled axial RF ion guide. The RF ion guide is simulated with q-factor of quad=0.4, a 0.005 V/mm axial driving field, a pressure of $6 \times 10^{-3}$ Torr $N_2$ and an injection energy of 5 eV.

It can be seen from FIG. 3A that the axial energy drops off exponentially as expected. The ions can be said to lose around half their initial axial energy by the time they reach the halfway point in the gas cell.

FIG. 3B is a plot of axial velocity against the normalised relative time in the gas cell, t/td. When plotted in this way, it is clear that the regime approximated by Eqn. 8, i.e. $t_d \gg mK/q$, is valid for typical gas cell lengths and pressures with relatively low injection energies. These conditions may be associated with minimising fragmentation in the gas cell, i.e. for transfer of intact precursor ions.

In cases where $t_d$ is comparable to or greater than mK/q approximate solutions can be obtained using other approaches including series expansions of the exponential terms.

In accordance with various embodiments a correction or calibration routine may be provided which accounts for the transit time of parent or precursor ions across one or more devices interspersed between an ion mobility separation exit 11 and an orthogonal acceleration Time of Flight mass analyser. It is contemplated that the intermediate devices include, but are not limited to, electrostatic ion focusing optics, mass to charge ratio filtering quadrupoles and RF confined ion guides, ion funnels or gas cells with axial propulsion via travelling waves, axial DC fields or gas flows. It is also contemplated that more than one of each device type can be disposed within the beam path. The equations described previously (and in the following) can be incorporated into such routines or algorithms as a basis for correcting or calibrating measured drift time against ion mobility or collision cross section. The Time of Flight mass to charge ratio analyser provides accurate mass to charge ratio measurements which can be used in equations/algorithms to correct the measured drift times.

For example, with reference to FIG. 1, if the ion mobility separation device 5 is a traditional drift tube, ions will exit in order of decreasing ion mobility according to the classic ion mobility separation drift tube equation (Eqn. 9a). For travelling wave ion mobility separation devices, the relationship between time and mobility is well approximated by Eqn. 9b:

$$T(K) = \frac{L_{IMS}}{KE} \qquad (9a)$$

$$T(K) = \frac{L_{IMS}}{K^\alpha f(\overline{E})} \qquad (9b)$$

wherein $L_{IMS}$ is the length of the ion mobility separation drift tube, K is the ion mobility and E is the electric field applied along the length of the drift tube and wherein $\alpha$ and $f(\overline{E})$ are dependent on the geometry and parameters of the travelling wave.

For simplicity, embodiments will primarily be described by considering drift tube-based ion mobility separation (Eqn. 9a) only. However, the general principles also apply to any other ion mobility separation devices, i.e. travelling wave based ion mobility separation (Eqn. 9b).

In the instrument of FIG. 1, after the ion gate 4 is opened ions pass through the ion mobility separation device 5, transit through the transfer region 6 and focussing optics region 7 and arrive at the orthogonal acceleration Time of Flight mass analyser 8 at a time:

$$T_{measured} = \frac{L_{IMS}}{KE} + T_{TR2} + T_{FO} \qquad (10)$$

The transit times $T_{TR2}$ and $T_{FO}$ can be determined using the equations described above. For example, if the intermediate pressure transfer region 6 is a travelling wave device of length $L_{TW}$ and is operated with a travelling wave velocity S then ions arrive at the Time of Flight mass analyser 8 at a time:

$$T_{measured} = T(K, m/q) = \frac{L_{IMS}}{KE} + \frac{L_{TW}}{S} + A\sqrt{m/q} \qquad (11a)$$

This equation can be rearranged to give the true drift time as:

$$T_{DT} = \frac{L_{IMS}}{KE} = T_{measured} - \frac{L_{TW}}{S} - A\sqrt{m/q} \quad (11b)$$

The measured ion arrival times at the ion detector and the mass to charge ratio determined by the Time of Flight mass analyser 8 can be substituted into Eqn. 11 to determine the accurate or corrected drift time, $T_{DT}$.

The Time of Flight mass analyser 8 may determine the mass to charge ratio of ions, for instance, using the acquisition system described in U.S. Pat. No. 6,992,283 (Micromass). The technique thus allows the measured drift times for each component in the two dimensional drift time-mass to charge ratio space to be corrected to account for both the time offset due to ions traversing the intermediate pressure transfer region 6 and the mass to charge ratio dependent time offset resulting from ions traversing the focussing optics 7. The true drift times may then be used to determine ion mobility or collisional cross section ("CCS") either directly from the true drift time calculations or via calibration routines that relate true drift times to ion mobilities or CCSs.

As a second example, the embodiments shown in FIG. 2 can be considered wherein the further transfer region 10 comprises a RF gas cell and ions are driven through the cell by an axial field. Components then arrive at the orthogonal acceleration Time of Flight mass analyser 8 at a time:

$$T_{measured} = \frac{L_{IMS}}{KE} + T_{TR2} + T_Q + T_{TR3} + T_{FO} \quad (12)$$

Under the conditions described above in relation to Eqn. 8, Eqn. 12 becomes:

$$T(K, m/q) = \frac{L_{IMS}}{KE} + \frac{L_{TW}}{S} + B\sqrt{m/q} + \frac{L_{GC} + K_{GC}^2 E_{GC} \frac{m}{q} - U_0 K_{GC} \frac{m}{q}}{K_{GC} E_{GC}} + A\sqrt{m/q} \quad (13)$$

wherein $E_{GC}$, $L_{GC}$ and $K_{GC}$ are the axial electric field in the gas cell, length of the gas cell and ion mobility within the gas cell respectively and $U_0$ is the velocity that ions enter the gas cell and is dependent on mass to charge ratio.

The coefficients A and B can again be determined from first principles, from simulations or from calibration experiments. If the coefficients have been derived from a calibration experiment they may appear as a single coefficient i.e. A+B.

Again, Eqn. 13 can be rearranged to reveal the true drift times, $L_{IMS}/KE$, and hence a routine can be developed to correct the drift time measurements. To solve this equation knowledge (or calibration) of the mobilities of ions within the gas cell is required. It may be desired that the ion mobility in the gas cell is a scaled value of the ion mobility in the ion mobility separation device, which generally requires similar gasses to be provided in both devices.

Some examples of parameters that may be calibrated directly include time offsets and the coefficients A and B. As another example, the ion mobility $K_{GC}$ appearing in Eqn. 13 depends on the gas cell pressure and temperature. If this pressure or temperature is unknown, then the mobility $K_{GC}$ could be replaced by $$K_{GC} = C_{GC} \frac{q}{\sqrt{\mu} \Omega_d}$$

where $\Omega_d$ is the same cross section that appears in the expression for the mobility K in the ion mobility separation cell, μ is the reduced mass and $C_{GC}$ is a parameter to be calibrated.

In another embodiment, techniques are provided that can be used to calculate the arrival time of ions at intermediate devices along the beam path. In this way, the accuracy and precision of device control within an ion mobility separation cycle may be improved. For example, WO 2013/140132 (Micromass) describes a method of controlling a resolving quadrupole within an ion mobility separation cycle to improve selectivity and duty cycle. The method relies on switching the quadrupole to isolate one or more specific parent or precursor ions as they arrive at the quadrupole within an ion mobility separation cycle. In the geometry shown in FIG. 2 of the present application, ions arrive at the quadrupole device 9 at a time intermediate between the times at which they exit the ion mobility separation device 5 and the measured time at orthogonal acceleration Time of Flight mass analyser 8. Using the equations presented above, this time can be determined as:

$$T(K) = \frac{L_{IMS}}{KE} + \frac{L_{TW}}{S} \quad (14)$$

Other approaches that control intermediate devices within an ion mobility separation cycle, such as enhanced duty cycle ("EDC") approaches and those described in U.S. Pat. No. 7,586,088 (Micromass) and U.S. Pat. No. 7,622,711 (Micromass) will also benefit from this approach. For example, U.S. Pat. No. 7,622,711 (Micromass) describes a method of improving the fragmentation efficiency of a population of parent or precursor ions by varying the fragmentation energy as a function of ion mobility separation cycle time. For optimum performance, this requires knowledge of the arrival time at the gas cell. Referring again to the instrument geometry of FIG. 2 of the present application, the gas cell may be part of transfer region 10. Ions arrive at this region after traversing the ion mobility separation device 5, intermediate pressure transfer region 6 and quadrupole mass filter 9 at a time:

$$T(K, m/q) = \frac{L_{IMS}}{KE} + \frac{L_{TW}}{S} + B\sqrt{m/q} \quad (15)$$

The various embodiments described above are concerned with the measurement of intact parent or precursor ions for determining accurate and precise ion mobility measurements and/or for improving instrument control within an ion mobility separation cycle. However, the geometries illustrated in FIGS. 1 and 2 are also capable of producing fragment ions at various positions along the beam path for performing MSMS, $MS^e$ or $HDMS^e$ type analysis.

For instance, U.S. Pat. No. 6,992,283 (Micromass) describes an approach for acquiring post ion mobility separation fragment ions which allows fragment ion profiles to be generated along the drift time dimension of separation. It is important to note generally that in hybrid instruments employing post-ion mobility separation fragmentation, the arrival times of fragment ions may be used to determine the parent or precursor ion mobility or drift time. The fragment ion drift time profiles are related to but not identical to the corresponding parent or precursor ion profiles, and the differences predominantly manifest themselves as differences in arrival times at the orthogonal acceleration Time of Flight mass analyser. Thus, using fragment ions in this manner may reduce the accuracy or precursor ion drift time measurements. This is firstly because the fragment ions arrive at the orthogonal acceleration Time of Flight mass analyser at a time dependent on both the mass to charge ratio of the parent or precursor ions and the mass to charge ratio of the fragment ions and secondly because the time and position of the fragmentation process within the fragmentation device is not accounted for.

In accordance with a further embodiment, a technique may be provided that accounts for additional ion transit times within a hybrid instrument containing a fragmentation or reaction device. In this case, both the transit time of precursor ions across one or more devices interspersed between an ion mobility separation exit 11 and the fragmentation device, and the transit time of resulting fragment ions across any devices disposed between the fragmentation device and the ion detector may need accounting for. The drift times of parent or precursor ions can be corrected or calibrated against ion mobility or collision cross section based on the measurement of fragment ions at the ion detector. Again, the devices contemplated include, but are not limited to, electrostatic ion focusing optics, quadrupole mass to charge ratio filters and RF confined ion guides, funnels or gas cells with axial propulsion via travelling waves, axial DC fields or gas flows. It is also contemplated that more than one of each device type may be disposed within the beam path. The ion detection system may provide accurate mass to charge ratio measurements of fragment ions for use in routines based on the previously described equations. Parent or precursor ion mass to charge ratios may be determined or selected, for instance, using a quadrupole mass filter or other mass or mass to charge ratio analysis device.

For example, referring to FIG. 2, if parent or precursor ions of mass to charge ratio M/Q are caused to fragment in a gas cell in transfer region 10 to produce fragment ions of mass to charge ratio m/q, parent or precursor ions arrive at the gas cell at a time after the ion gate 4 is opened:

$$T(K, M/Q) = \frac{L_{IMS}}{KE} + \frac{L_{TW}}{S} + B\sqrt{M/Q} \quad (16)$$

The transit time of the ion beam across any devices disposed downstream of the gas cell is however related to the fragment ion properties. For example, the transit time across the focusing optics 7 is:

$$T_{FO}(m/q) = A\sqrt{m/q} \quad (17)$$

The difference between fragment ions profiles and their corresponding precursor ion profiles for the transition M/Q→m/q can be partially accounted for by combining these equations to give:

$$T(K, M/Q, m/q) = \frac{L_{IMS}}{KE} + \frac{L_{TW}}{S} + B\sqrt{M/Q} + A\sqrt{m/q} \quad (18)$$

Eqn. 18 only partially accounts for the differences between fragment ion profiles and corresponding parent or precursor ion profiles because the exact time taken to transit the gas cell is still unknown. The fragmentation event may occur at an unknown position after an unknown period of time within the gas cell. Furthermore, the step of fragmentation is generally structurally dependent. This is illustrated with reference to FIG. 4.

Figure 4:
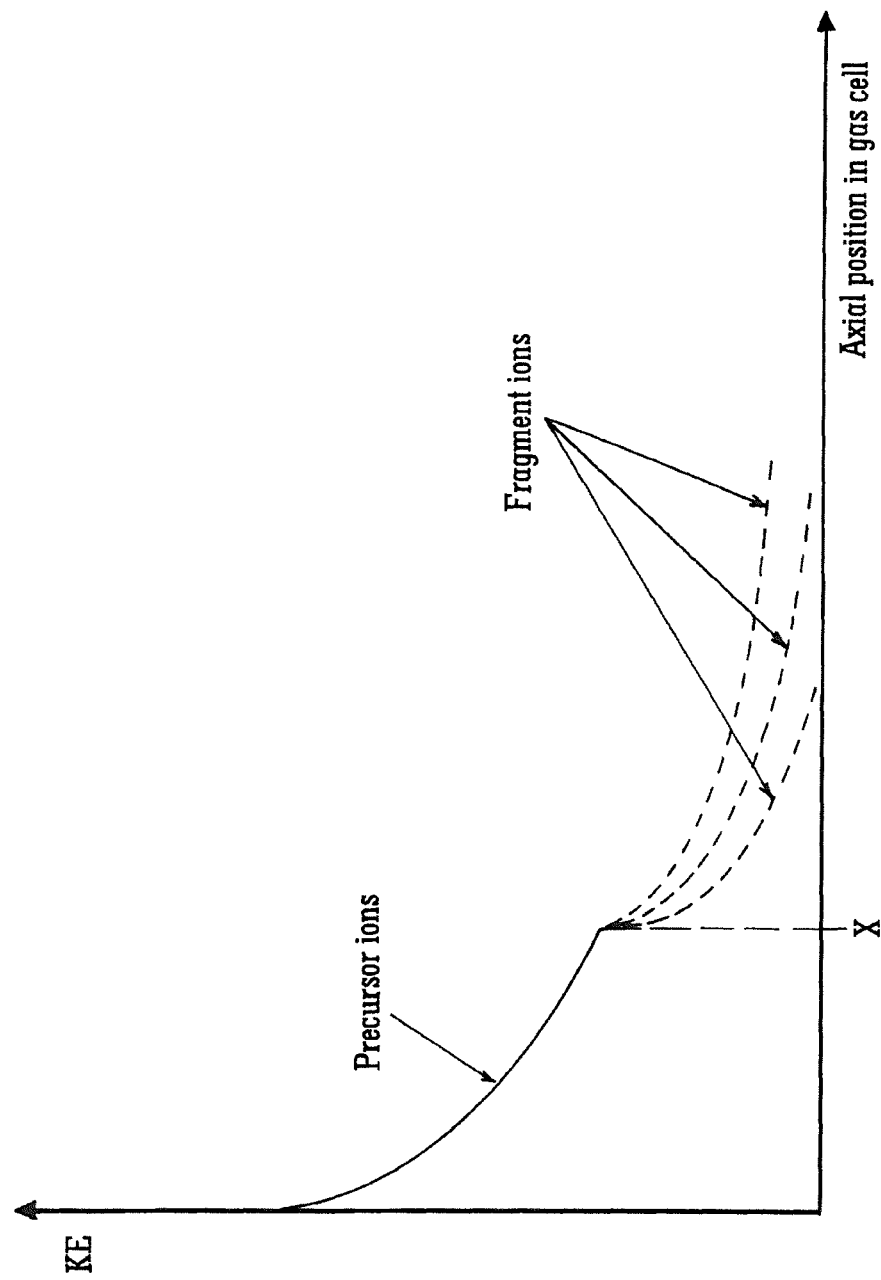
FIG. 4 schematically shows ion kinetic energy as a function of axial position within a gas-filled fragmentation cell.

FIG. 4 depicts the kinetic energy of ions as a function of axial position in a gas cell. In FIG. 4, parent or precursor ions are injected into the gas cell at elevated energies. As the precursor or parent ions start to collide with the gas the precursor or parent ions gradually lose kinetic energy (whilst gaining internal energy). At some point, shown as X in FIG. 4, the parent or precursor ions fragment to produce a number of fragment or product ions having different mass to charge ratios. These fragment ions continue to lose kinetic energy, albeit at a different rate as described in the previous equations and as illustrated in FIG. 4. It is emphasized that FIG. 4 is schematic and presented for illustrative purposes only. In reality the fragment ions may themselves undergo further fragmentation provided they have sufficient energy. Furthermore, the production of fragment ions may correlate with axial position. For example, higher mass to charge ratio fragment ions may tend to form closer to one end of the gas cell than lower mass to charge ratio fragment ions.

It can, however, be appreciated from FIG. 4 that these effects introduce certain time delays. Although these time delays are generally unknown or partially unknown, they are reproducible for a given parent-fragment transition. These time delays may in turn yield useful structural information or may be useful in library searches values.

In another embodiment effective arrival times of parent-fragment transitions at the ion detection system, e.g. the orthogonal acceleration Time of Flight mass analyser can be determined. In this embodiment fragment ions are produced and their profiles determined in a similar manner to that described above, but the parameters of the first device (e.g. the ion mobility separation device) may be varied to allow at least two measurements of each transition. By varying parameters of an ion mobility separation device, unknown and ion mobility separation-independent factors, such as those described above in relation to FIG. 4, can be cancelled and/or corrected for. In particular, the time for a particular precursor-fragment transition to transit a reaction or fragmentation device can be determined and a suitable correction or calibration routine may be provided.

For example, referring to FIG. 2 and Eqn. 9a above, changing the axial field applied along the length of the drift tube ion mobility separation device 5 results in a change in the transit time across the ion mobility separation device 5 for ions having a given ion mobility. As described above, the ion transit time for a particular transition through a gas cell (disposed within intermediate transfer region 10) may include an unknown but reproducible time delay. The time delays introduced by the fragmentation process may mean that the ion arrival times at the mass analyser 8 cannot be accurately predicted based on mass to charge ratio or ion mobility alone.

In these circumstances, Eqn. 9a can be modified to include an unknown (or partially unknown) delay term, D, as per Eqn. 20:

$$T(K) = \frac{L_{IMS}}{KE} + D \tag{20}$$

The delay term, D, can be determined and hence accounted for by varying the strength of the drift field, E, between at least two measurements. An exemplary method of correcting for these delay terms will now be described.

Figure 5:
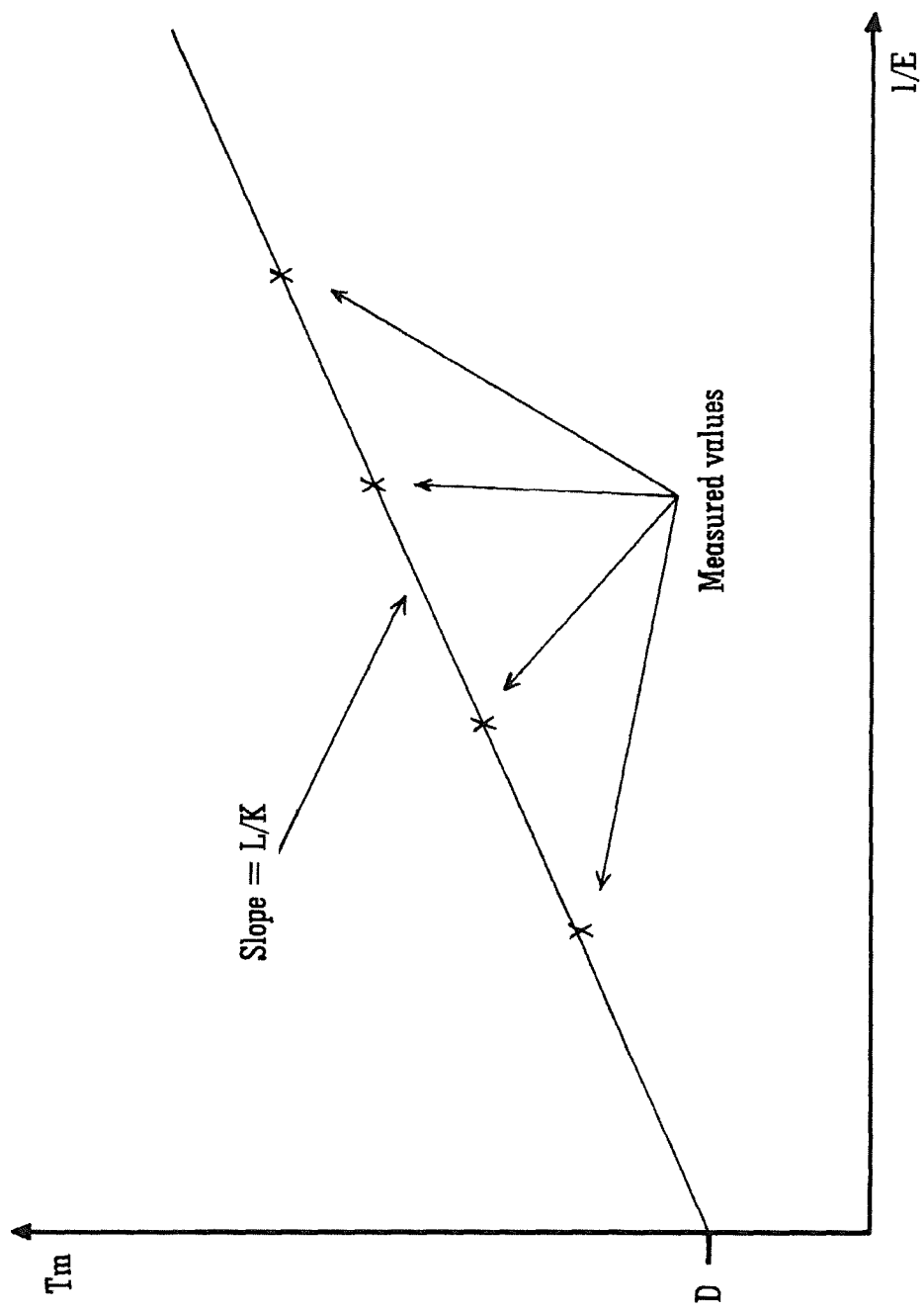
FIG. 5 shows the measured fragment ion drift time as a function of varying ion mobility separation inverse field strength for a single transition.

FIG. 5 shows a plot of measured fragment ion drift time, i.e. the measured arrival time at the detector, against varying 1/E for a particular precursor-fragment transition. As per Eqn. 20, the slope of the line is inversely proportional to the ion mobility K of the precursor or parent ion.

Figure 6:
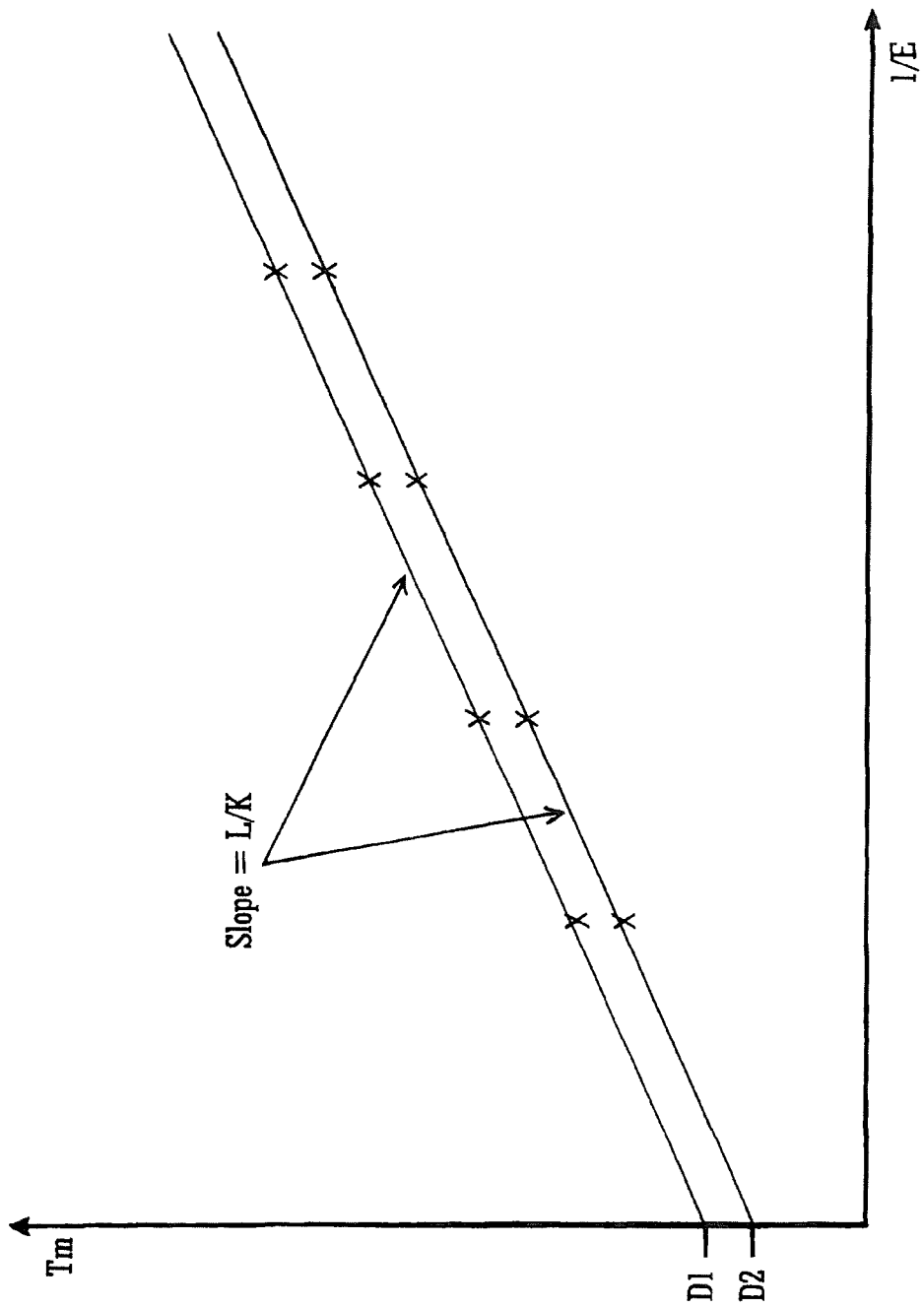
FIG. 6 shows the measured fragment ion drift time as a function of varying ion mobility separation inverse field strength for two transitions.

FIG. 6 is a similar plot for the same precursor or parent ion but for two different transitions i.e. different fragment ions. In FIG. 6 the slope of the two plots is the same indicating that the precursor or parent ion mobility is the same. The associated delay time for each plotted transition is the measured drift time at E=0 i.e. the y-intercept of FIG. 6.

It will be appreciated that the delay time, D, as defined in Eqn. 20, may include the transit time through a number of intermediate regions disposed between the exit 11 of the ion mobility separation device 5 and the mass analyser 8. Thus, the delay times may be partially known based on the mass to charge ratio of the precursor ions, the mass to charge ratio of the fragment ions or other deterministic transit times as described previously. In these cases, the known delays may be accounted for before calculations such as those shown in FIGS. 5 and 6 are performed. The skilled person will understand that any of the techniques described in this application may be combined in order to account for known terms. Once any known terms have been accounted for, the resulting delay times contain information related to the time taken for a precursor ion to fragment in the gas cell. As mentioned above, this information may prove useful by itself in, for example, structural determination and library searches.

Instead of varying the drift field, E, similar results can be obtained by varying the separation length, $L_{IMS}$, of the ion mobility separation device 5.

Figure 7:
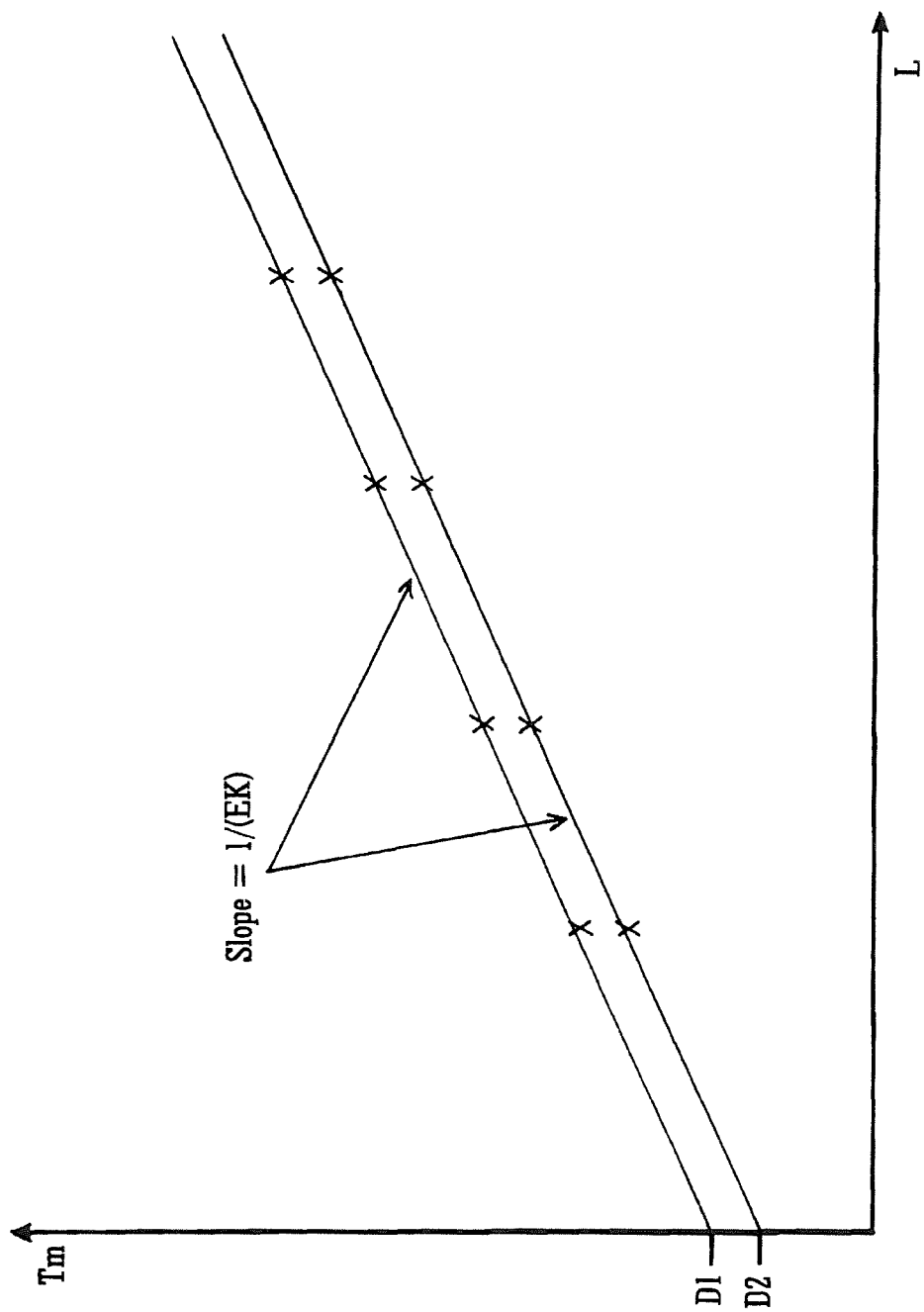
FIG. 7 shows the measured fragment ion drift time as a function of varying ion mobility separation length.

FIG. 7 is a plot of fragment arrival time against varying separation length. Four measurements have been taken at different separation lengths. Again, two different transitions of the same precursor or parent ion are plotted. The slope is proportional to 1/K and the delay times can be readily determined from the y-intercept.

As described above, referring e.g. to Eqns. 5-8, shortening the length of the ion mobility separation device may in some cases introduce additional known delays which may be accounted for.

Varying the length of the ion mobility separation device rather than the axial field may advantageously avoid disturbing the stability and/or precision of the potentials applied to adjacent upstream or downstream devices. The ion mobility separation length can be increased in a closed loop ion mobility separation device by changing the number of passes. Alternatively/additionally, the ion mobility separation length can be changed by adjusting the ion gate position or by using non-separating travelling waves to transmit ions over certain subsections of the ion mobility separation device.

It is important to note that changing either the drift field or the length of the ion mobility separation device will fundamentally affect its resolution. That is, components which can be separated in drift time at one drift field/length may not be separated at a lower field/shorter length.

The coupling of ion mobility separation to a high resolution orthogonal acceleration Time of Flight mass spectrometer with an acquisition system like that described in U.S. Pat. No. 6,992,283 (Micromass) provides improved analytical peak capacity, thus alleviating the effects of reduced ion mobility separation resolution. This is due to the partially orthogonal relationship between precursor or parent ion mobility and precursor or parent mass or mass to charge ratio. Pure drift time peak profiles, i.e. for single, not interfered with components, can be constructed provided that the components are sufficiently separated in the mass or mass to charge ratio dimension. Additionally, the act of post-ion mobility separation fragmentation may further increase the peak capacity, due to the substantially orthogonal relationship between precursor ion mobility and fragment ion mass or mass to charge ratio. Whilst the described method focuses on drift tube based ion mobility separation, the same approach may be adopted for travelling wave based ion mobility separation. This requires an understanding of the relationship between drift times through the travelling wave ion mobility separation device and various travelling wave parameters such as wave length, wave profile, wave speed and wave amplitude. Shvartsburg et al, Anal. Chem. 2008, 80, 9689-9699, derives analytical expressions for these relationships. As an example, Shvartsburg shows that under certain conditions the drift time though a travelling wave ion mobility separation device is given by:

$$T(K) = \frac{L_{IMS}S}{K^2\overline{E}^2} \tag{21}$$

wherein S is the wave speed and $\overline{E}^2$ is the average of $E^2$ over the waveform of the travelling wave, which is directly related to its amplitude.

Again, unknown or partially known, i.e. deterministic, delays can be accounted for using this relationship in a similar manner to that described above. In this regime, the amplitude can be varied and the measured drift time can be plotted against the inverse square wave amplitude as shown in FIG. 8.

Figure 8:
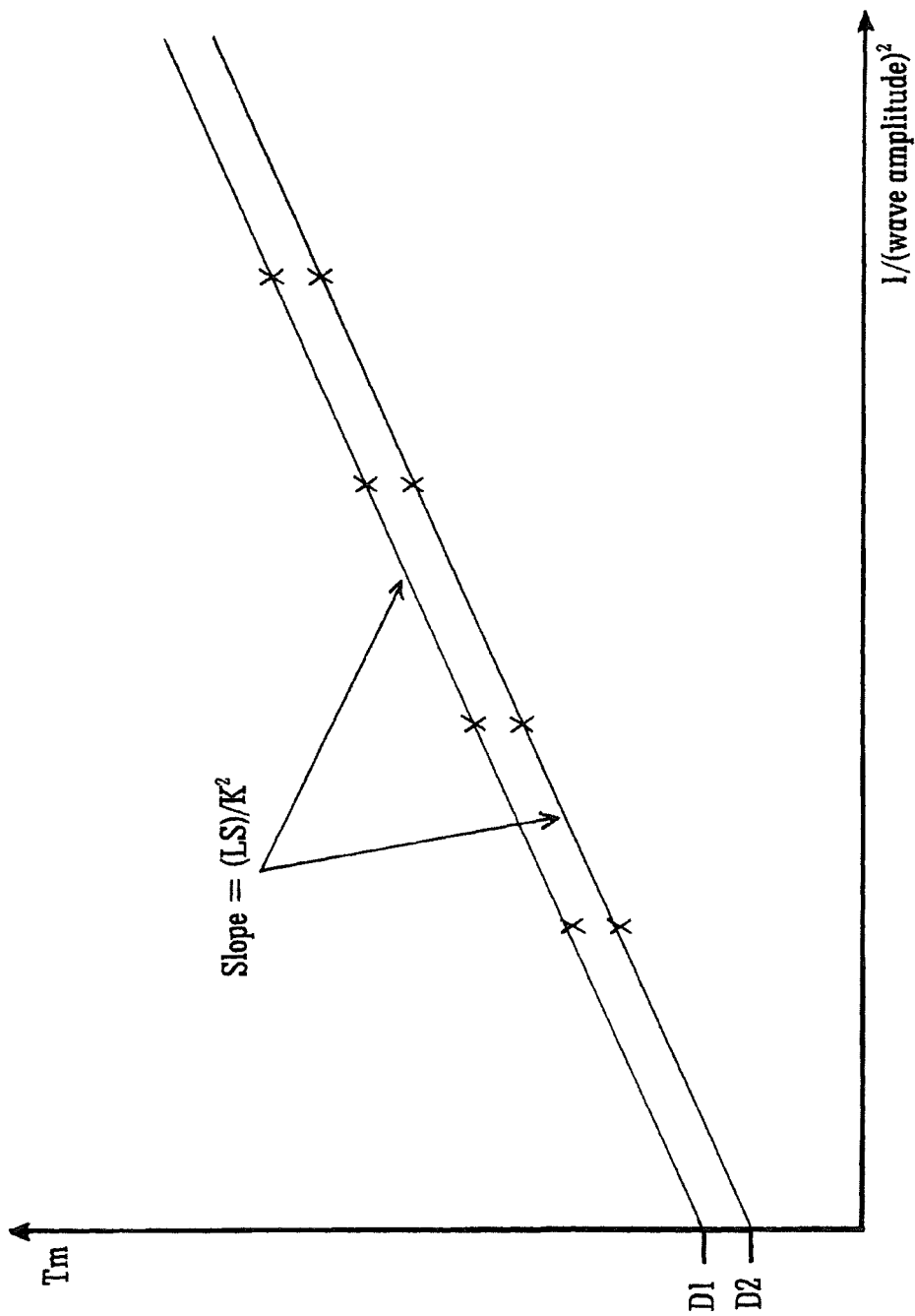
FIG. 8 shows the measured fragment ion drift time as a function of inverse square wave amplitude.

In FIG. 8, the slope is proportional to $1/K^2$ and an unknown delay time, D, can be determined from the y-intercept.

Eqn. 21 only applies for certain conditions. Deviating from the regime associated with Eqn. 21 will therefore result in a different relationship between T and K. However, the general approach can still be adopted.

In the approaches described above and illustrated in FIGS. 5-8, the ion mobility K is determined from the slope or gradient of certain plots. The skilled person will understand however that the measurements can be analyzed equally using any other suitable method. For example, the parameters can be determined using simple arithmetic as illustrated below.

Consider two measurements of arrival time at different field values, (T1, E1) and (T2, E2), for a device described by Eqn. 20. For ions of mobility K, subtracting T2 from T1 gives:

$$T1(K) - T2(K) = \frac{L_{IMS}}{KE1} + D - \frac{L_{IMS}}{KE2} - D \quad (22)$$

which can be rearranged to allow a direct determination of K:

$$\frac{L_{IMS}}{K} = \frac{T1(K) - T2(K)}{\frac{1}{E1} - \frac{1}{E2}} \quad (23)$$

The approaches described above generally allow determination of ion mobility, drift time or gradient. For instruments employing post-ion mobility separation fragmentation, the determination of parent or precursor ion mobility or drift time can be used to assign or link fragment ions to their corresponding precursor ion or to other related fragment ions.

The skilled person will understand that any of the above described techniques can be advantageously combined. For instance, the ion mobility or drift time of parent or precursor ions may be determined using Eqn. 13 and the precursor or parent ion mobility or drift time for resulting fragment ions determined using Eqn. 23. Fragment ions can then be assigned to other fragment ions and/or precursor or parent ions based on these values. For example, if two fragment ions are determined to have the same precursor or parent ion mobility, then they may be assigned to the same precursor or parent ion. Referring to FIG. 6, for instance, the two plotted transitions have the same slope and hence the same precursor or parent ion mobility. A transition having a different slope would indicate a different precursor or parent ion mobility and hence a different precursor or parent ion.

The embodiments described above use an orthogonal acceleration Time of Flight as the mass to charge ratio analyser and detector. However, the techniques are not limited in this respect. It is possible to couple ion mobility separation devices to other mass analysers including quadrupole-based mass analysers and ion traps such as an ORBITRAP® or an electrostatic mass analyser arranged to generate an electrostatic field having a quadro-logarithmic potential distribution. The techniques disclosed above are also applicable to such instruments. Accurately determining the time at which ions arrive at any particular device may facilitate moving the transmission window of a quadrupole at the correct time or accurately selecting a drift time region for filling an ion trap. In the case of a resolving quadrupole, the selected mass to charge ratio region will provide the mass to charge ratio values for the calibrations or corrections described above.

In some instances the deterministic transit times include both precursor or parent ion mobility and precursor or parent mass to charge ratio dependent terms. In practice, these two parameters are correlated for a given charge state such that either value can be approximated by measurement of the other. This correlation may provide sufficient accuracy or precision for implementing the techniques described herein.

Although the embodiments described above relate to the context of ion mobility separation, other fast separation techniques may also benefit from the described approaches. For instance, the techniques described generally above may advantageously be used with fast traps with post-ejection fragmentation.

Although the present invention has been described with reference to particular embodiments, it will be understood by those skilled in the art that various changes in form and detail may be made without departing from the scope of the invention as set forth in the accompanying claims.

The invention claimed is:

1. A method of mass spectrometry comprising:
separating ions temporally in a first device;
analysing the mass or mass to charge ratio of said ions or of product or fragment ions derived from said ions in a mass or mass to charge ratio analyser disposed downstream of said first device;
obtaining a first set of drift times for said ions through said first device by measuring ion arrival times;
determining the transit time of said ions and/or of said product or fragment ions through one or more intermediate regions or devices disposed between said first device and said mass to charge ratio analyser; and
switching or adjusting the operating condition of one or more devices disposed between said first device and said mass or mass to charge ratio analyser based on the determined transit time of ions through said one or more intermediate regions or devices.

2. A method as claimed in claim 1, wherein the step of separating ions temporally in said first device comprises separating ions according to ion mobility, wherein said one or more devices disposed between said first device and said mass or mass to charge ratio analyser comprise one or more of: (i) a quadrupole mass filter or a quadrupole device; (ii) an electrostatic lens; (iii) an ion guide; (iv) a fragmentation or reaction device; or (v) a collision cell.

3. A method as claimed in claim 1, wherein the transit time of ions through said one or more intermediate regions or devices is a function of mass or mass to charge ratio and/or ion mobility.

4. A method as claimed in claim 1, further comprising determining the transit time of ions through one or more intermediate regions or devices disposed between said first device and said mass to charge ratio analyser using the mass or mass to charge ratio analysis.

5. A method as claimed in claim 1, further comprising determining the transit time of ions through one or more or each of a plurality of intermediate regions or devices.

6. A method as claimed in claim 1, comprising maintaining said first device at a higher pressure than said mass or mass to charge ratio analyser, and maintaining said one or more intermediate region or device at an intermediate pressure between that of said first device and said mass or mass to charge ratio analyser.

7. A method as claimed in claim 1, wherein said step of analysing the mass or mass to charge ratio of ions is performed using a Time of Flight or orthogonal acceleration Time of Flight mass spectrometer, and optionally further comprising operating said Time of Flight mass spectrometer in a nested acquisition mode.

8. A method as claimed in claim 1, further comprising:
after the step of separating ions temporally in the first device, causing ions to fragment or react; and
determining the transit time of parent or precursor ions through an intermediate region or device disposed upstream of said fragmentation or reaction device and/or the transit time of fragment or product ions through an intermediate region or device disposed downstream of said fragmentation or reaction device.

9. A method as claimed in claim 8, comprising determining the drift time of parent or precursor ions through said first device using the mass or mass to charge ratio of corresponding fragment or product ions.

10. A method as claimed in claim 8, comprising determining the transit time of a precursor-fragment transition through a fragmentation or reaction device.

11. A method as claimed in claim 8, further comprising assigning fragment or product ions to their corresponding parent or precursor ion or to other related fragment or product ions on the basis of a determined transit time, drift time, ion mobility or gradient.

12. A method as claimed in claim 1, further comprising varying one or more parameters of said first device to determine said transit times.

13. A mass spectrometer comprising:
a first device for separating ions temporally;
a mass or mass to charge ratio analyser disposed downstream of said first device;
one or more intermediate regions or devices disposed between said first device and said mass or mass to charge ratio analyser; and
a control system comprising a processor configured:
(i) to obtain a first set of drift times for said ions through said first device by measuring ion arrival times;
(ii) to determine the transit time of said ions and/or of said product or fragment ions through one or more intermediate regions or devices disposed between said first device and said mass to charge ratio analyser; and
(iii) to switch or adjust the operating condition of one or more devices disposed between said first device and said mass or mass to charge ratio analyser based on the determined transit time of ions through said one or more intermediate regions or devices.

14. A method of mass spectrometry comprising:
separating ions temporally in a first device;
analysing the mass or mass to charge ratio of ions in a mass or mass to charge ratio analyser disposed downstream of said first device;
determining the transit time of ions through an one or more intermediate regions or devices disposed between said first device and said mass to charge ratio analyser; and
switching or adjusting the operation of one or more devices disposed between said first device and said mass or mass to charge ratio analyser based on the determined transit time of ions through said one or more intermediate regions or devices.

15. A method as claimed in claim 14, comprising, after the step of separating ions temporally in the first device, causing ions to fragment or react, and further comprising determining the transit time of parent or precursor ions through an intermediate region or device disposed upstream of said fragmentation or reaction device and/or the transit time of fragment or product ions through an intermediate region or device disposed downstream of said fragmentation or reaction device.

16. A method as claimed in claim 15, comprising determining the drift time of parent or precursor ions through said first device using the mass or mass to charge ratio of corresponding fragment or product ions.

17. A method as claimed in claim 15, comprising determining the transit time of precursor-fragment transition through a fragmentation or reaction device; and/or further comprising assigning fragment or product ions to their corresponding parent or precursor ion or to other related fragment or product ions.

* * * * *